(12) United States Patent
Fossan

(10) Patent No.: US 9,889,309 B2
(45) Date of Patent: Feb. 13, 2018

(54) METHOD AND APPARATUS FOR DETECTING A SHOCK APPLIED TO A PATIENT DURING CPR

(71) Applicant: Laerdal Medical AS, Stavanger (NO)

(72) Inventor: Helge Fossan, Stavanger (NO)

(73) Assignee: Lærdal Medical AS, Stavanger (NO)

( * ) Notice: Subject to any disclaimer, the term of this patent is extended or adjusted under 35 U.S.C. 154(b) by 0 days.

(21) Appl. No.: 15/039,859

(22) PCT Filed: Dec. 1, 2014

(86) PCT No.: PCT/EP2014/076043
§ 371 (c)(1),
(2) Date: May 27, 2016

(87) PCT Pub. No.: WO2015/096954
PCT Pub. Date: Jul. 2, 2015

(65) Prior Publication Data
US 2017/0021182 A1 Jan. 26, 2017

Related U.S. Application Data

(63) Continuation of application No. 14/139,707, filed on Dec. 23, 2013, now abandoned.

(51) Int. Cl.
*A61N 1/00* (2006.01)
*A61N 1/39* (2006.01)

(52) U.S. Cl.
CPC ......... *A61N 1/3925* (2013.01); *A61N 1/3937* (2013.01)

(58) Field of Classification Search
CPC ........................... A61N 1/3925; A61N 1/3937
USPC ............................................................ 607/8
See application file for complete search history.

(56) References Cited

U.S. PATENT DOCUMENTS

| | | | |
|---|---|---|---|
| 5,078,134 A * | 1/1992 | Heilman | A61B 5/6831 600/508 |
| 5,540,724 A | 7/1996 | Cox | |
| 6,280,461 B1 * | 8/2001 | Glegyak | A61N 1/39 607/5 |
| 2009/0076559 A1 * | 3/2009 | Libbus | A61N 1/046 607/6 |
| 2009/0295326 A1 | 12/2009 | Daynes et al. | |
| 2011/0202100 A1 * | 8/2011 | Tan | A61H 31/005 607/6 |

FOREIGN PATENT DOCUMENTS

| | | |
|---|---|---|
| EP | 0546666 | 6/1993 |
| WO | WO93/16759 Y | 9/1993 |

* cited by examiner

*Primary Examiner* — Christopher D Koharski
*Assistant Examiner* — Philip C Edwards
(74) *Attorney, Agent, or Firm* — Christian D. Abel

(57) ABSTRACT

Method and apparatus for detecting electric energy delivered to the heart of a body when performing defibrillation. The method comprises the steps of applying a defibrillator with electrodes placed on opposite sides of the heart; applying an apparatus on the body and between said electrodes for detecting and measuring electric and/or magnetic fields; performing defibrillation by delivering electric energy to the body; detecting electric energy running through the heart with said apparatus, and indicating electric energy applied to the heart. The apparatus for performing the method comprises detection and indications means for performing the method.

11 Claims, 4 Drawing Sheets

METHOD AND APPARATUS FOR DETECTING A SHOCK APPLIED TO A PATIENT DURING CPR

The present disclosure describes examples of methods and apparatuses for monitoring CPR defibrillation. Examples of methods and apparatuses are described for detecting an electric shock applied to a patient without communicating with the defibrillator used.

BACKGROUND

CPR (Cardiopulmonary resuscitation) is an emergency procedure for manually preserving the blood circulation of a person in cardiac arrest. Cardiac arrest means that the normal circulation of blood has stopped due to failure of a normal heart function, typically that the heart fails to contract effectively.

Lack of blood circulation is critical since delivery of oxygen to the body is prevented. Lack of oxygen to the brain is very critical and will cause loss of consciousness, which in turn will result in abnormal or absent breathing. If cardiac arrest is not treated within five minutes brain damage will most likely follow.

CPR generally involves chest compressions at least 5 cm deep and at a rate of at least 100 per minute in an effort to create artificial circulation by manually pumping blood through the heart. CPR is often combined with electric shock treatment by performing defibrillation.

Defibrillation includes delivering a therapeutic dose of electrical energy to the heart with a device called a defibrillator. The purpose is to restore a normal heart rhythm by depolarizing a critical mass of the heart muscle. Defibrillators can be external or implanted, depending on the type of device used or needed. Some external units, known as automated external defibrillators (AEDs) automate the diagnosis such that lay responders or bystanders are able to use them successfully with little or no training at all.

The connection between a defibrillator and a patient consists of a pair of electrodes that are placed on the patient such that an electric shock passes through the heart muscle.

FIG. 1 is an illustration showing a typical electrode placement on a body 10 used during defibrillation where one electrode 100, 105 is placed on each side of the heart 110 such that the electric shock 115, symbolized as dashed lines, will pass through the heart.

Applying electric shock to a body is well known, but knowing if the body actually has received an electric shock and the efficiency of this without measuring this directly in the body is not known.

Even if a defibrillator indicates that a shock has been given it does not guarantee that the shock has been applied to a patient. There is a risk of causing injury to a patient when using a defibrillator. This is due to possible electrical resistance between electrodes and body resulting in possible burning of a patient. Minimization of electrical resistance for decreasing the impedance to a chest is normally done by using electricity conductive gel.

Knowing that a shock has been applied to a patient is thus an important factor when considering further application of shock treatment.

SUMMARY OF THE INVENTION

The present disclosure describes examples of methods for detecting electric energy delivered to the heart of a body when performing defibrillation. An example method may include:

applying a defibrillator with electrodes placed on opposite sides of the heart;

applying an apparatus on the body and between said electrodes, the apparatus configured to detect and measure electric and/or magnetic fields;

performing defibrillation by delivering electric energy to the body;

detecting electric energy running through the heart with said apparatus, and indicating electric energy applied to the heart.

The disclosure also describes examples of apparatuses for detecting electric energy delivered to the heart of a body when performing defibrillation. An example apparatus comprises a receiver circuit operable to detect electric field and/or magnetic field and mechanisms for indicating electric energy applied to the heart.

Further features of the apparatus are defined in the claims.

BRIEF DESCRIPTION OF DRAWINGS

Examples will now be described in detail with reference to the figures where.

DETAILED DESCRIPTION

As generally described above, the state of the art may have drawbacks in that there is a need for a detection method and apparatus for measuring with a high degree of certainty that a shock has been applied to a patient, and where this is performed without being connected to the defibrillator used and without measuring this directly in the body.

Figure 1:
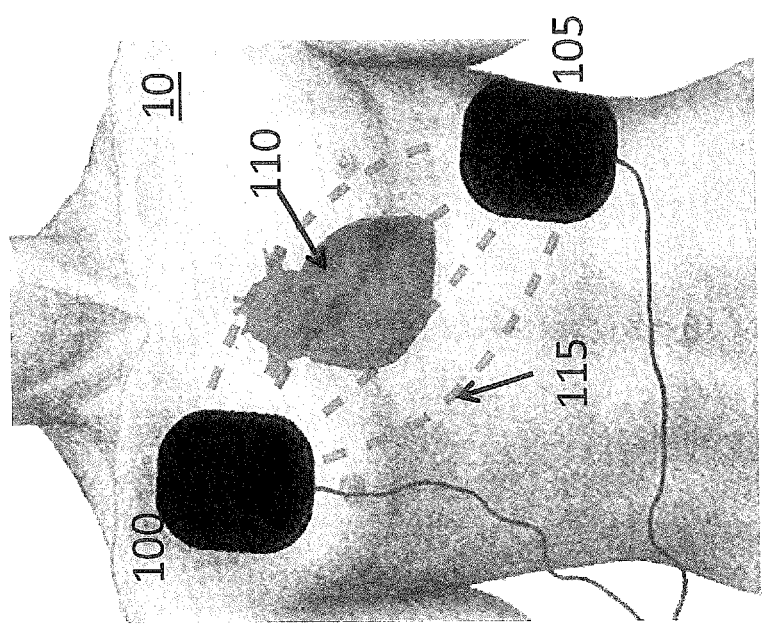
FIG. 1 show a typical electrode placement used during defibrillation.
Figure 2:
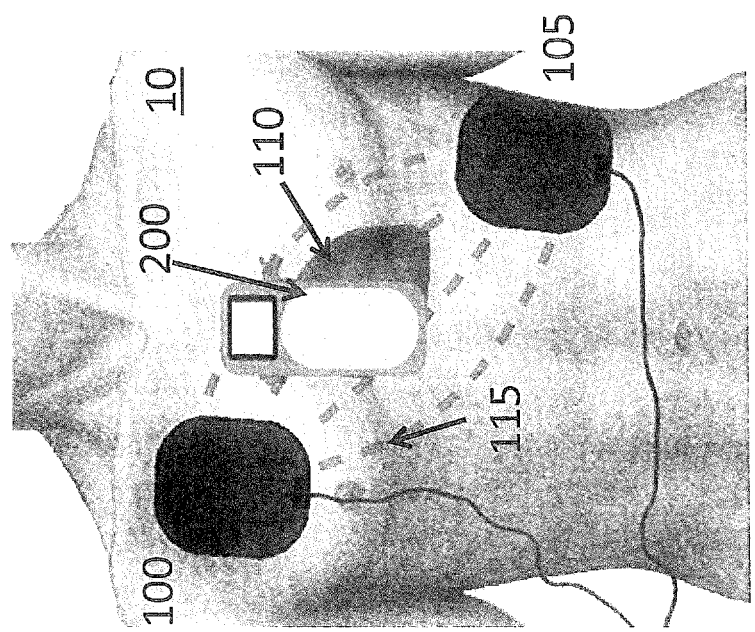
FIG. 2 shows the placement of the inventive apparatus for detecting if a shock has been applied to a body.

FIG. 1 shows a typical electrode placement used during defibrillation, while FIG. 2 shows the placement of the inventive apparatus 200, relative to the electrodes 100, 105, for detecting if a shock 115 has been applied to a body 10.

Figure 3:
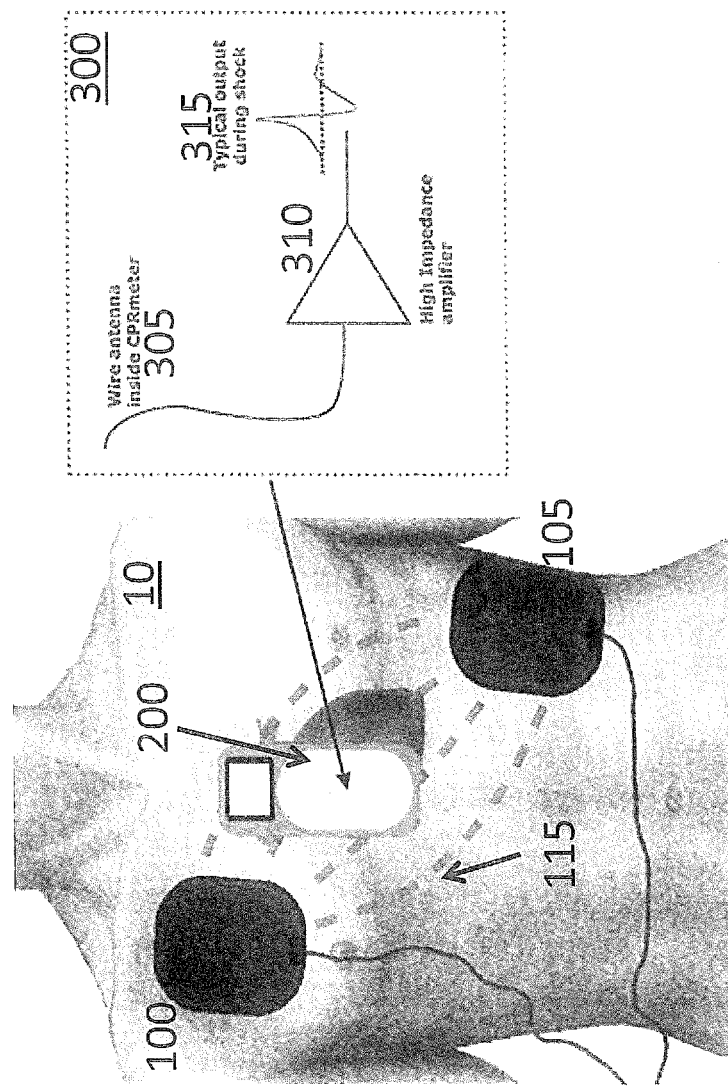
FIG. 3 shows a detection circuit comprised in the apparatus for detecting electric field.

FIG. 3 shows one embodiment of the apparatus according to the disclosure with a detection circuit 300 for detecting electric field and electrical level shift that occurs during shock. The detection circuit 300 may include a wire antenna 305 and a high impedance amplifier 310. The electric shock applied may be biphasic and current and polarity may reverse during the shock. Typical voltages may be >2 kV, and currents may be >15 A (peak values). Voltage change in the body may cause charge transfer to the high impedance antenna inside the apparatus. The output from the amplifier may be a positive or negative waveform 315 as illustrated in FIG. 3. Detection may be triggered when detecting a waveform exceeding set voltage levels, positive or negative.

Detection of Hall effect is also feasible.

Before a shock is applied, the body 10 and the apparatus 200 will have ground levels that are almost the same. During the shock, the area underneath the apparatus 200 will change voltage level since the apparatus 200 is not placed in the electrical center of the two electrodes 100, 105; it is closer to the sternum electrode 100. The apparatus 200 will also be close to the current flow 115 in the tissue underneath the apparatus 200.

Figure 4:
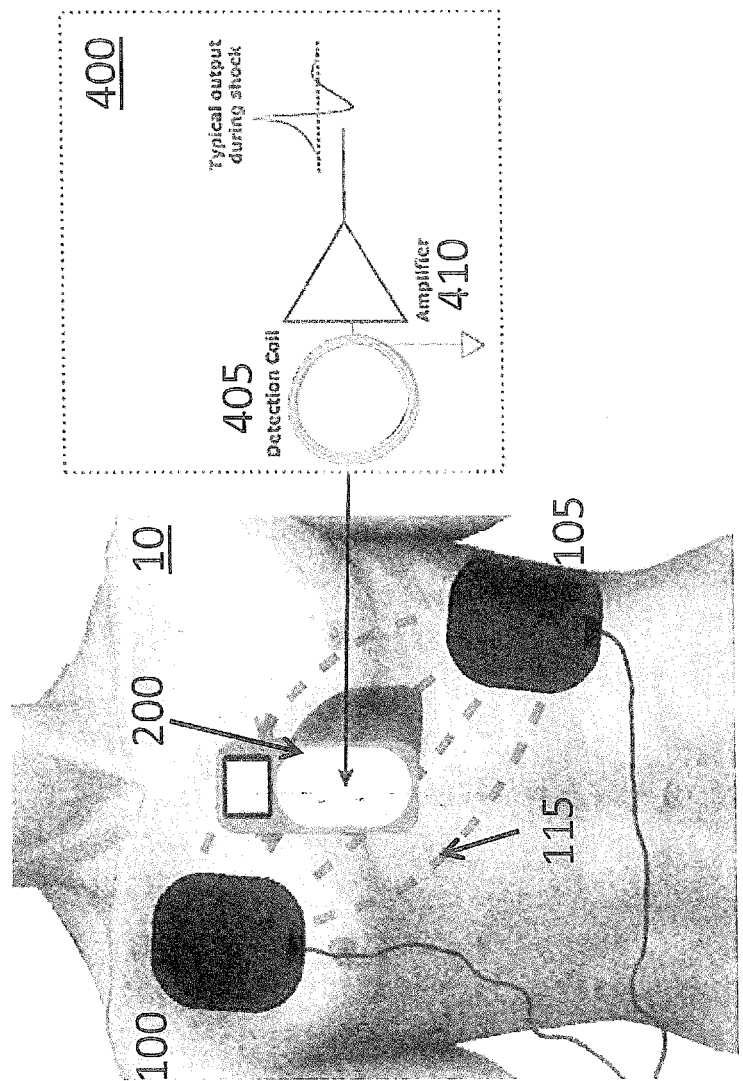
FIG. 4 shows a detection circuit comprised in the apparatus for detecting magnetic field.

FIG. 4 shows another embodiment of the apparatus according to the disclosure comprising a detection circuit 400 for detecting magnetic field generated during a shock. A pickup coil, or detection coil 405 may be oriented such that the magnetic field lines from the current through the tissue, i.e. the axis through the coil should align with the axis between the electrodes for detection with maximum sensitivity. The output from an amplifier 410 may be a positive or negative waveform as illustrated. Detection is achieved by detecting a waveform exceeding set voltage levels, positive or negative.

In the example embodiments above an antenna 305 may be used for picking up changes in electric field due to voltage changes, and a pickup coil 405 may be used for detecting magnetic field.

For a skilled person it is obvious that other mechanisms for detecting electric and magnetic fields are feasible, e.g. electromagnetic pulse detection, Hall field detection, etc.

The apparatus for detecting electric energy delivered to the heart 110 of a body 10 when performing defibrillation is in one embodiment of the disclosure a standalone device with power supply and a receiver circuit operable to detect electric field and/or magnetic filed as well as a mechanism for indicating electric energy applied to the heart. In one embodiment the mechanism may be visual, e.g. including a display. In another embodiment the mechanism may be sonic, e.g. including a speaker. In yet another embodiment, the mechanism may be visual and sonic, e.g. including a display and speaker. A user may then be given feedback for electric energy applied to the heart by way of light and sound.

In one embodiment the apparatus further comprises an accelerometer for detecting body motion. This will contribute to better detection accuracy of a shock applied.

One embodiment of the disclosure that may be advantageous when performing CPR is an apparatus further comprising a CPR meter. This may provide a compact and a very efficient tool for performing CPR and at the same time have full control of shocks applied to a patient.

The apparatus may comprise in one embodiment timing and storing mechanisms (e.g. one or more clocks and/or memory devices) for storing the time for detection of a shock. This may be performed either with reference and relative to the episode used, or by a real time clock implementing the absolute time of defibrillation.

The apparatus according to an embodiment may further comprise a transmitter for transmitting data related to time and shock detected.

A method for detecting electric energy delivered to the heart of a body when performing defibrillation may comprise several steps.

The first step may be applying a defibrillator with electrodes placed on opposite sides of the heart.

The second step may be applying an embodiment of an apparatus of the disclosure on the body and between said electrodes for detecting and measuring electric and/or magnetic fields.

The next step may be performing defibrillation by delivering electric energy to the body.

The next step may be detecting electric energy delivered to the heart by using the apparatus comprising a detector for detecting electric and/or magnetic field(s). Measuring of electric energy in the form of electric and/or magnetic fields in one embodiments may be combined with motion detection for detecting movements in the body.

Detection of a shock by detecting electric field or magnetic field may not by itself necessarily be proof of a shock received by the body. Other electric devices in the surrounding area can cause electric disturbance which can lead to false detection of a shock.

The accuracy of detection of a shock may be significantly improved if an accelerometer is included in the measurements for detecting body motion associated with the shock. In most cases a defibrillator shock will cause significant muscle contraction resulting in a measurable movement.

In one embodiment of the disclosure, measurement of movement is performed. An accelerometer included in an apparatus may provide movement measurements that may be combined with electric and/or magnetic field measurements. Preferably all these types of measurement may be combined in order to increase the accuracy of the detection of a shock with electric energy delivered to the heart.

In one embodiment, the apparatus used for detecting and measuring electric and/or magnetic fields may be a wireless device comprising a CPR meter. This may be an advantageous combination since is CPR meter is often used when performing CPR. A CPR meter may provide important feedback to the user related to compression depth and speed.

We claim:

1. A method for detecting electric energy delivered to a heart of a body when performing defibrillation, the method comprising:
    applying a defibrillator with electrodes placed on opposite sides of the heart;
    applying an apparatus on the body and between said electrodes, said apparatus comprising a stand-alone device separate from the defibrillator and configured to detect and measure electric and/or magnetic fields;
    performing defibrillation by delivering electric energy to the body;
    detecting electric energy running through the heart with said apparatus, and
    indicating electric energy delivered to the heart by means of said apparatus.

2. The method according to claim 1, wherein the apparatus for detecting and measuring electric and/or magnetic fields is wireless.

3. The method according to claim 1 or 2, wherein the apparatus used for detecting and measuring electric energy comprises a CPR meter.

4. The method according to claim 1 or 2, wherein the apparatus used for detecting and measuring electric energy is further configured to detect body motion.

5. The method according to claim 4, wherein the measured electric field, magnetic field and body motion are combined for detecting and indicating electric energy applied to the heart.

6. An apparatus for detecting electric energy delivered to the heart of a body when performing defibrillation by a defibrillator, the apparatus comprising a stand-alone device separate from the defibrillator and further comprising:
    a receiver circuit operable to detect an electric field and/or a magnetic field when placed between electrodes of the defibrillator delivering an electric shock, and
    an indicator for indicating electric energy delivered to the heart.

7. An apparatus according to claim 6, further comprising an accelerometer for detecting a movement in the body.

8. An apparatus according to claim 6 or 7, further comprising a power supply and wherein the apparatus is configured to operate wirelessly.

9. An apparatus according to claim 6 or 7, further comprising a CPR meter.

10. An apparatus according to claim 6 or 7, further comprising a visual and/or a sonic indicator for indicating electric energy applied to the heart.

11. An apparatus according to claim 6 or 7, comprising a transmitter configured to transmit data to indicate electric energy applied to the heart.

* * * * *